United States Patent [19]

Bernard

[11] Patent Number: 5,522,008
[45] Date of Patent: May 28, 1996

[54] DEVICE FOR HEATING AND VAPORIZING A VAPORIZABLE MODULE

[76] Inventor: Costello J. Bernard, 68 Lover's La., Princeton, N.J. 08540

[21] Appl. No.: 213,958

[22] Filed: Mar. 16, 1994

[51] Int. Cl.$^6$ ........................................ H05B 3/26
[52] U.S. Cl. ........................................ 392/392; 392/390
[58] Field of Search ........................ 392/390, 392, 392/395; 43/129; 422/123, 125, 305, 306; 219/543; 29/619, 620

[56] References Cited

U.S. PATENT DOCUMENTS

| | | |
|---|---|---|
| 2,513,919 | 7/1950 | Costello . |
| 2,691,716 | 10/1954 | Wellens ........................ 392/390 |
| 2,756,322 | 7/1956 | Sibert ........................... 422/123 |
| 2,942,090 | 6/1960 | Diehl ............................ 219/390 |
| 3,534,148 | 10/1970 | Barge ........................... 219/543 |
| 3,748,438 | 7/1973 | Costello ....................... 392/390 |
| 3,800,020 | 3/1974 | Parfet . |
| 4,084,079 | 4/1978 | Costello . |
| 4,689,103 | 8/1987 | Elarde . |
| 4,725,712 | 2/1988 | Schroeder .................... 392/390 |
| 4,731,520 | 3/1988 | Glucksman et al. ......... 392/390 |
| 4,849,605 | 7/1989 | Nakamori ..................... 219/543 |
| 4,849,606 | 7/1989 | Martens ........................ 392/390 |
| 5,091,958 | 2/1992 | Sakamoto ..................... 381/150 |
| 5,136,684 | 8/1992 | Lonker et al. . |
| 5,213,523 | 5/1993 | Hygema et al. ............. 392/390 |
| 5,220,636 | 6/1993 | Chang .......................... 392/390 |
| 5,226,840 | 7/1993 | Wojtanek . |
| 5,259,111 | 11/1993 | Watanabe . |

*Primary Examiner*—Teresa J. Walberg
*Assistant Examiner*—Sam Paik
*Attorney, Agent, or Firm*—Louis Weinstein

[57] ABSTRACT

A vaporizing device including a heating unit having a pair of electrical connector terminals staked to a substantially rigid substrate having a serpentine resistance type heating element printed thereon and electrically connected to the terminals. An insulating conformal layer coats the heating element, wicking into the interstices of the region between said electrical terminals and the openings in the substrate receiving the terminals to significantly enhance the structural strength of the device. This provides an inexpensive and yet sturdy and rugged vaporizing device which may be discarded after each use.

12 Claims, 3 Drawing Sheets

DEVICE FOR HEATING AND VAPORIZING A VAPORIZABLE MODULE

FIELD OF THE INVENTION

The present invention relates a heating device for heating a vaporizable material and to a method for producing same and more particularly to a method for producing a heating device which, in addition to being a rugged and sturdy unit, is inexpensive and may be discarded after each use.

BACKGROUND OF THE INVENTION

Deodorants and insect and pest repellants have become quite popular for use in deodorizing and/or protecting rooms, including bathrooms, of homes, hospitals, factories, office buildings and the like. In addition to deodorizers and repellants employing wicks which are exposed to the air within a room being deodorized, and sprays, such as aerosol sprays, electrically heated deodorizers and repellant devices have recently been developed as a very popular alternative for the aforementioned deodorizers.

A variety of such devices are presently in the marketplace and typically comprise a housing containing a vaporizable module. A pair of electrical terminals project from a rear surface of the housing for electrical connection into a standard wall socket typically providing 115 volt a.c. power. The a.c. source energizes a resistance heater for heating a scent module, for example, to release a pleasant aroma or essence into the atmosphere so long as the heater element is energized.

When a scent module is dissipated, it is discarded and replaced with a new module. Scent modules are available for purchase as refills, enabling the heating element unit to be used over and over again.

Conventional devices have a number of disadvantages. Firstly, the heating device housing must be provided with a releasable closure device to permit access to the scent module compartment for removal and replacement of a scent module, causing the structure of the device to be relatively complex and bulky and further causing the unit to protrude away from the wall containing the electrical socket into which the heating unit is inserted, thus presenting a potential obstruction to passersby as well cleaning apparatus (brooms, sweepers, vacuum cleaners and the like). In addition, the complex structure which requires moving, or at least movable parts, significantly increases production costs. In addition, substantially unlimited reuse of the heating device significantly contributes to the possible deterioration and even faulty and possible dangerous operation of the heating device. Users are typically unaware of deterioration or weakening of the device, thereby subjecting the user to potential harm.

BRIEF DESCRIPTION OF THE INVENTION

The present invention is characterized by comprising a novel heating device structure and a method for producing such heating devices which are characterized by comprising a design that can be produced at a cost which is significantly less than the cost of producing conventional heating devices thereby enabling heating devices produced according to the method of the present invention to be discarded after the vaporizable capsule housed therein is exhausted, i.e. leading to the development of a heating device which may be discarded after exhaustion of a block or module, if desired.

The heater assembly of the present invention comprises a polymer resistor element printed upon one surface of an insulating substrate utilizing conventional printed circuit techniques. The resistor-type heating element is electrically connected to an electrical power source by means of a pair of metal blades or terminals which are inserted through openings provided in the insulating substrate, which blades have projections that are mechanically crimped to the substrate in order to make good electrical contact with the heating element.

The crimping operation is followed by the step of coating the resistor element with an insulating resin to protect the surface of the resistor element and the exposed surface of the crimped metal portion of the terminals which protrude through the substrate. In one preferred embodiment, a housing is molded about the heater assembly and vaporizable module, effectively eliminating any moving or movable parts. The conformal layer, in addition to providing an insulating coating for the heater element and crimped projections, wicks into the interstices between the openings in the substrate and the blades to significantly enhance the resistance to atmospheric corrosion between the crimped projections and the substrate which enhances the integrity of the electrical path between the electric terminals and the resistance-type heater element as well as imparting structural strength to the unified substrate and electrical blades to significantly enhance the safe use of the scent or repellant emitting device.

With the need for a removable and replaceable cover eliminated, the molded package becomes quite compact and has an extremely low profile, yielding a housing which projects outwardly from a wall socket by a distance which is significantly less than those encountered in conventional electrical scent emitting devices.

In a preferred embodiment, the scent module is provided with flutes or grooves which cooperate with slot-like openings within the housing to provide a chimney effect for the emission of the airborne vapor.

In an alternative embodiment, the heating element may be snap-fitted into a slot-like receptacle within the housing to lock the heating element subassembly therein. The housing cover is snap-fittingly mounted thereto after insertion of the vaporizable module.

OBJECTS OF THE INVENTION

It is therefore one object of the present invention to provide a novel electrical-type vaporizing device incorporating a heating element subassembly of significantly enhanced mechanical and electrical strength, and a method for producing same.

Still another object of the present invention is to provide a low cost, electrical-type vaporizing device and a method for producing same and which permits the production of such units at significantly reduced cost, enabling the production of units capable of being discarded after one use.

Still another object of the present invention is to provide a novel electrical-type vaporizing device incorporating a heater element formed on an insulating substrate through the employment of printed circuit techniques and connected to a pair of electrical blades or terminals adapted for insertion into a conventional two terminal electric outlet and further including a conformal protective layer of a suitable polymer which provides insulation for the resistance-type heating element and exposed surfaces of crimped portions of the electrical terminals and which further wicks into the inter-

3 stices between the substrate and the terminals to impart significant structural strength to the assembly.

Still another object of the present invention is to provide a method for producing vaporizing devices of the type described above.

Still another object of the present invention is to provide a novel electrical-type vaporizing device comprising a one-piece, permanently sealed housing to prevent tampering either during or after use thereof.

Still another object of the present invention is to provide a novel electrical-type vaporizing device utilizing a fluted vaporizable module which cooperates with elongated slots provided in the housing of the vaporizing unit to provide a "chimney" effect.

BRIEF DESCRIPTION OF THE FIGURES

The above, as well as other objects of the present invention will become apparent when reading the accompanying description and drawings in which:

FIG. 3b is a detailed view showing the manner in which a housing side wall supports a marginal edge of a substrate.

DETAILED DESCRIPTION OF THE INVENTION AND PREFERRED EMBODIMENTS THEREOF

Figure 1:
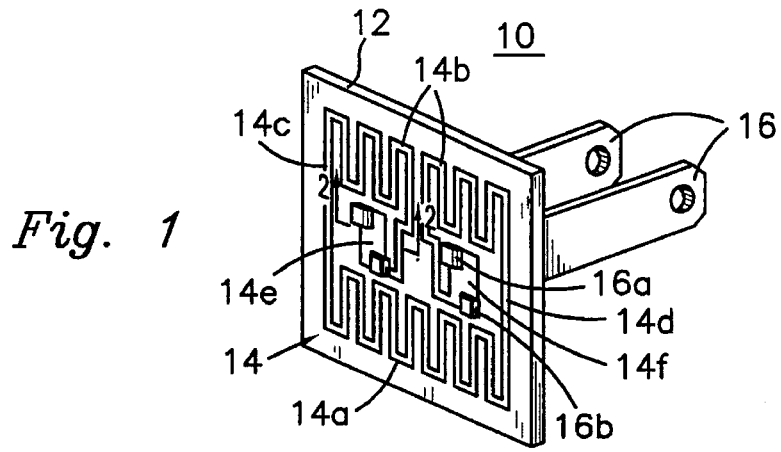
FIG. 1 is a perspective view of a heating device subassembly designed in accordance with the principles of the present invention.
Figure 2:
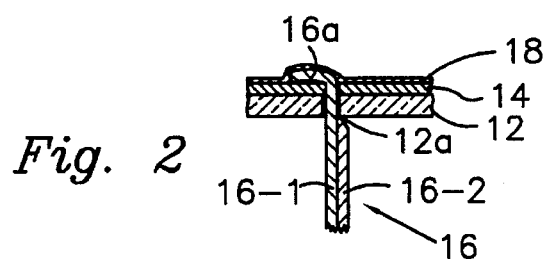
FIG. 2 show a sectional view of the mechanical and electrical connection between the insulating substrate and resistor-type heating element on the one hand and the electrical terminal on the other hand, looking in the direction of arrows 2—2 of FIG. 1.

FIGS. 1 and 2 show a heating element subassembly 10 designed in accordance with the principles of the present invention and comprised of a substantially rectangular-shaped insulating substrate 12 which is preferably formed of the same material utilized to produce printed wiring boards. The shape of the substrate 12 is not critical, the only criteria being that the substrate is large enough to accommodate the heating element and the terminals 16. A resistor-type heater element 14 is printed on one major surface of the insulating substrate 12 utilizing conventional techniques for creating such patterns on printed circuit boards and the like. The resistance-type heating element is preferably comprised of a polymer resistor element printed on the surface of the insulating substrate and is comprised of a first serpentine portion 14a joined to a second pair of serpentine portions 14b by substantially straight elongated pattern portions 14c and 14d. The facing ends of the adjacent, inner ends of the serpentine portions 14b extend downwardly and outwardly and terminate in a pair of terminal pads 14e and 14f which are each conductively electrically coupled to an electrical terminal 16 through crimped, bent-over ends 16a, 16b which form the portions of the electrical terminals that protrude through openings 12a provided in insulating substrate 12 for receiving the electrical connecting ends of the terminals 16. The projections 16a, 16b are bent over and firmly pressed into the associated terminal pad 14e, 14f to assure the provision of a good electrical conductive path. The size of the pads is not critical and the pads may be eliminated so long as the terminal ends provided are sufficient for electrical and mechanical engagement with an associated terminal 16.

An insulating resin 18 coats the exposed surfaces of projections 16a, 16b and the heater element to provide good electrical insulation, as well as corrosion resistance, therefor. In addition, the conformal insulating material wicks into the holes containing terminals 16 imparting significant structural strength to the joined terminals and the insulating substrate as well as providing the desired electrical insulation and corrosion resistance. The terminals are removably inserted into a conventional electrical outlet, not shown, having two elongated slot-like openings to receive said terminals.

Making reference to FIG. 5, a production method will now be described which lends itself to low cost production of a quality heating element of superior electrical and mechanical strength and integrity.

The production method utilized is based upon the use of multiple image printing and processing which enables the simultaneous production of a significant number of heating units.

Figure 5:
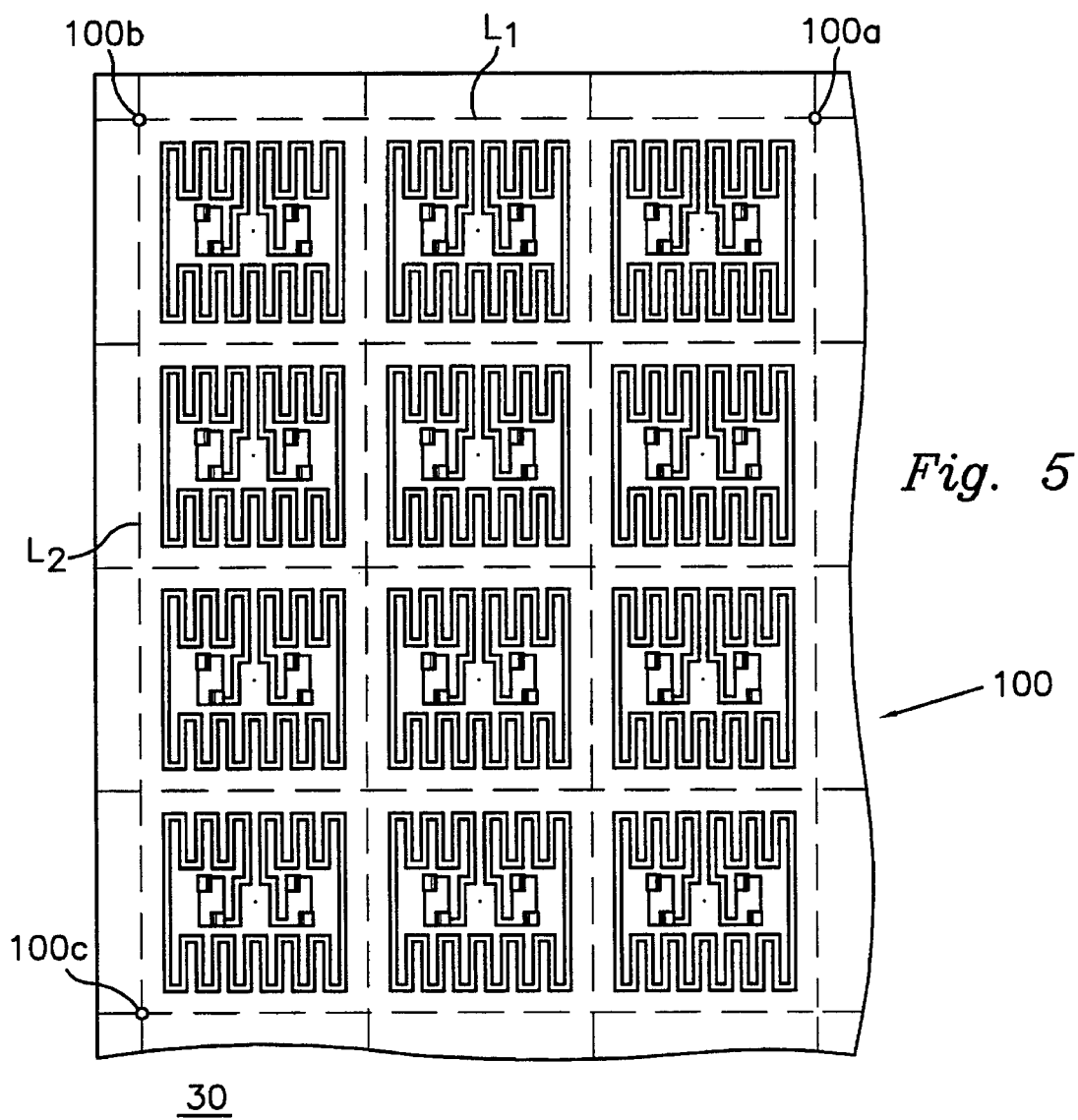
FIG. 5 shows a plan view of a substrate on which a plurality of heating unit subassemblies have been formed and which is useful in describing the techniques for simultaneously producing a plurality of such assemblies.

The process steps include the following:

Making reference to FIG. 5, a substrate panel 100 is cut to a suitable size which lends itself to economic production techniques. Utilizing a 24×24 inch square panel 100 to produce heating elements of a substantially square size shape of 1.25×1.25 inch square, the technique permits 361 such elements to be produced simultaneously per 24×24 inch square substrate 100. Smaller or larger size insulating substrates may be utilized, if desired. The size of the substrate of the individual heating element subassemblies (note FIG. 1, for example) may also be adjusted, if desired.

Three locating or pinning holes 100a, 100b and 100c are drilled into panel 100 to define a pair of datum lines L1 and L2 which are perpendicular to one another to provide repeatable reference points for mounting the board 100 to equipment (not shown) for performing successive processing steps, thereby assuring proper registration with the equipment used in moving from one processing step to the next.

With the panel 100 in proper registration, resistor patterns are simultaneously formed for each heater element unit utilizing conventional printed circuit techniques which, very briefly, typically include coating the entire insulating substrate with the polymer resistor material, coating the polymer resistor material with a etch resistant, covering the substrate with a pattern which, passes light only through regions of the resist which are to be etched away, etching away the areas of the resist exposed to light and thereby also etching away the polymer resistor material therebeneath and finally washing away the unexposed resist, leaving the desired polymer resistor patterns.

After the resistor patterns are formed, four holes are either punched or drilled in each individual substrate to accommodate the terminals 16a, 16b of the electrical contact terminals (see FIG. 1).

The substrate is then scored on both sides to provide the horizontal and vertical score lines $S_H$ and $S_V$.

Thereafter, a conductive contact terminal (i.e. blade) is inserted into each pair of holes provided for receiving same. The projections 16a, 16b of each conductive contact blade are firmly crimped, i.e. bent over and pressed into the surface of panel 100 containing the terminal pads of the resistor pattern to assure good electrical contact between each terminal and an associated resistor terminal pad.

The insulating coating which is preferably any one of polyurethane, polymer, Dymax 984LUF or other materials having similar properties is sprayed onto the surface of panel 11 bearing the resistor pattern, providing an electrical insulating coating for the resistor patterns as well as the exposed conductive surfaces of the crimped projections 16a, 16b. In addition, the coating material wicks into the openings receiving the electrical terminals to firmly fill and seal said openings and the interstices between the substrate 100 and the terminals 16, and thereby provide significant structural strength to the joined terminals 16 and each substrate 12. FIG. 2 shows the manner in which the insulating material has wicked into opening 12a to substantially fill any hollow or open regions between one terminal 16 and substrate 12, as well as providing an insulating coating and corrosion protecting coating over the resistor pattern 14 and the projections 16a and 16b.

After the insulating material is dried, electrical tests are performed to assure satisfactory electrical continuity and to further assure that the magnitude of the current through the resistance-type heating elements fall within an acceptable range.

Thereafter, the individual heating units 10 (see FIG. 1) are separated from one another by breaking the units apart from one another along the score lines $S_H$ and $S_V$, whereupon the individual units are ready to be assembled into the finished product.

Figure 3B:
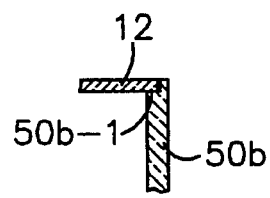
FIG. 3b shows a sectional view of one side wall of the housing of FIG. 3a looking in the direction of arrows 3b—3b and further showing the manner in which the substrate of the heating device subassembly mounts thereon.
Figure 3:
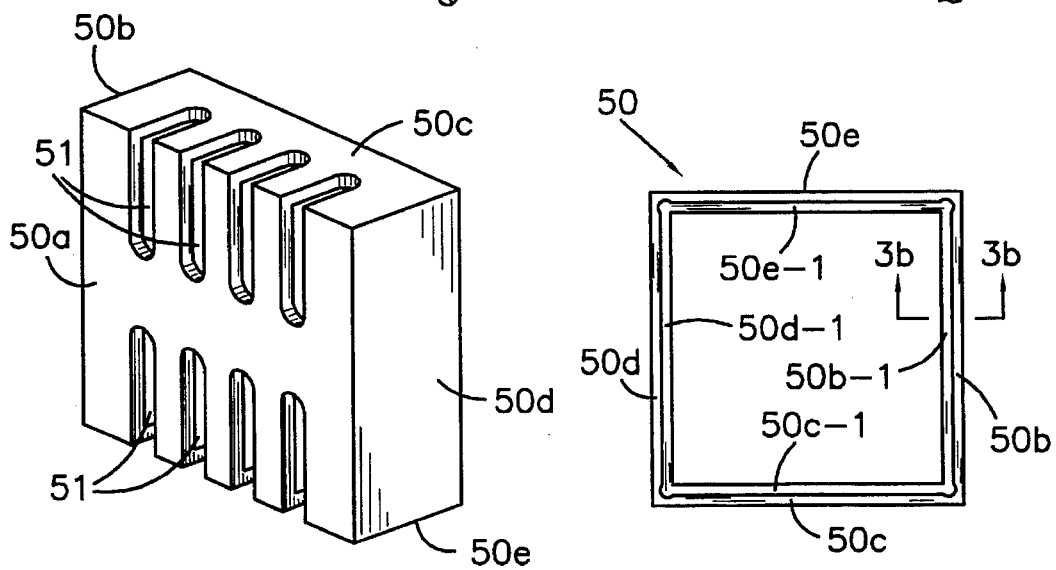
FIG. 3 shows a perspective view of a molded housing for use with the heating device subassembly of FIG. 1.
Figure 3A:
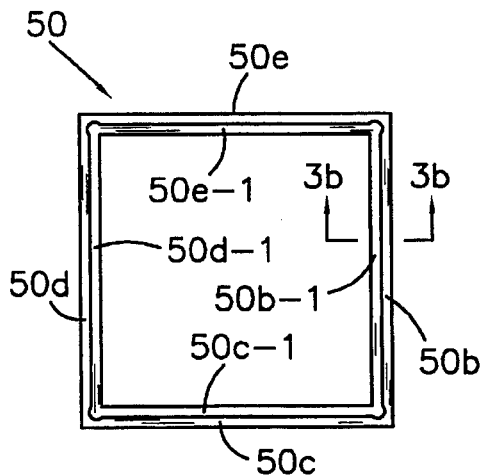
FIG. 3a shows a rear view of the housing of FIG. 3
Figure 4:
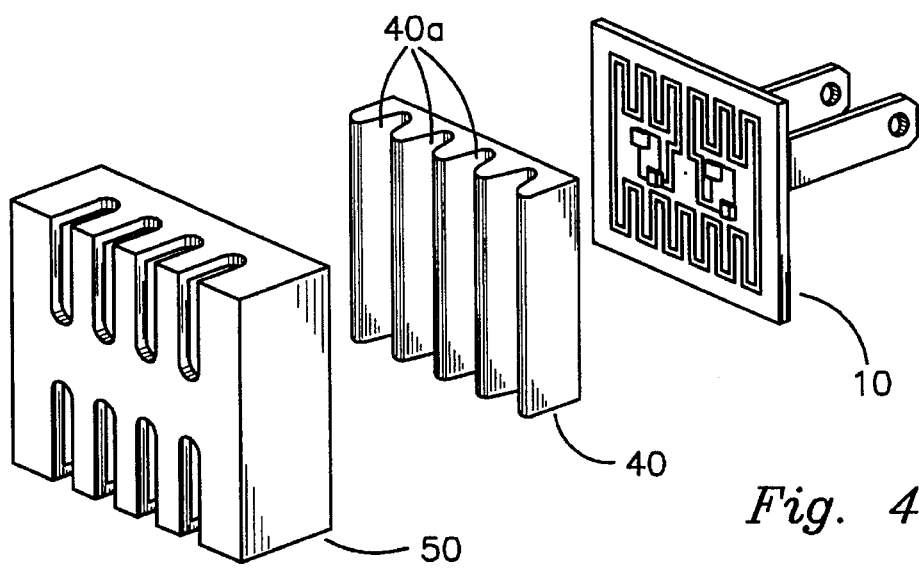
FIG. 4 shows a simplified, exploded, perspective view of the housing cover, heater unit subassembly and scent module forming the scent emitting device of the present invention.

FIG. 4 shows an exploded view of the components of the heater of a scent generating unit comprised of heating unit 10, a scent module 40 and a housing or cover 50. Cover 50 is shown in greater detail in FIGS. 3, 3a and 3b and is comprised of a front face 50a surrounded by four side walls 50b, 50c, 50d and 50e which define an open-ended hollow interior for receiving scent module 40. Elongated slots 51 are provided in housing 50, said slots extending along front face 50a and side walls 50c and 50e. The housing 50 may be used with other vaporizable modules, if desired.

Interiors of the side walls 50b through 50e are each provided with a shoulder 50b-1 through 50e-1, said shoulders each supporting a marginal edge of the heating element substrate 12, FIG. 3b showing the manner in which one marginal edge of substrate 12 is supported by shoulder 50b-1.

The housing 50 is preferably a molded member or alternatively may be machined in the configuration shown. The scent (or repellant) module 40 is inserted into the mold member whereupon the heater unit is positioned so that its marginal edges are each supported by an associated shoulder 50b-1 through 50e-1. The substrate may be secured to cover housing 50 by a suitable epoxy or glue or alternatively by application of heat or a solvent upon assembly of the components fusing the substrate and housing to one another thereby providing a finished unit which is quite rugged and compact and neither has nor requires any moving or movable parts. The superior structural strength of the heater unit subassembly 10 assures and enhances the integrity of the mechanical and electrical connections therein providing a device which may be installed and used safely.

The flutes 40a, comprising a plurality of elongated grooves, provided in the front face of module 40, cooperate with the housing and the openings 51 in cover housing 50 to provide a chimney effect which facilitates delivery of the scented airborne vapors into the region surrounding unit 30. More particularly, as vapors are emitted from a "top" end air enters into the "bottom" end, creating the "chimney effect". The module 40 may alternatively be formed of a vaporizable solid material for use as an insect or pest repellant which may also incorporate a pleasing scent.

Figure 6A:
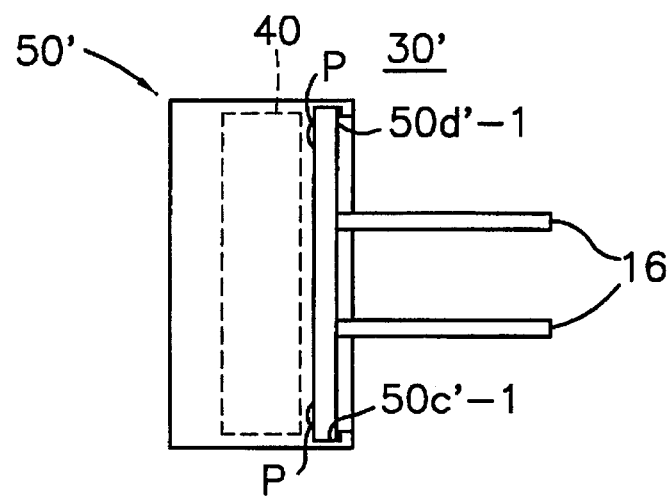
FIGS. 6a, 6b and 6c are views showing the manner in which a heating unit and a scent modular are installed within a housing.
Figure 6B:
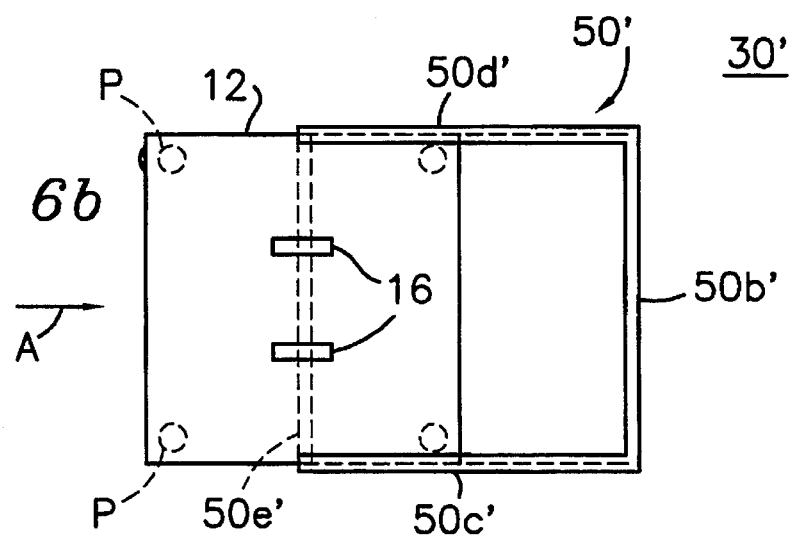
Figure 6C:
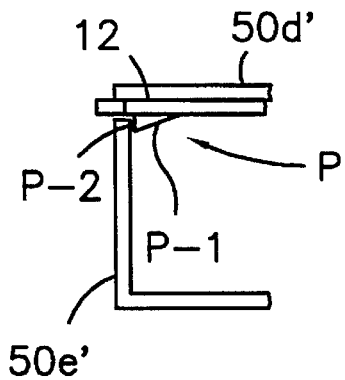

FIGS. 6a and 6b show still another preferred embodiment 30' of the present invention which utilizes a heating element subassembly 10' substantially similar to that shown, for example, in FIGS. 1 and 4 being modified only to provide a pair of locking protrusions P provided on one face thereof. Module 40 is substantially the same type as shown in FIG. 4. The cover housing 50' differs from the cover housing 50 of FIG. 4 in that the shoulders 50b-1 through 50e-1 are substantially eliminated, wall 50b' is a solid end wall while a portion of side wall 50e' is removed as shown best in FIG. 6a and parallel side walls 50c' and 50d' are provided with grooves 50d'-1 and 50c'-1 which slidably receive opposite parallel edges of the substrate 12. The substrate 12 is pushed into the substrate receiving groove 50d'-1 and 50c'-1 in a direction shown by arrow A as shown in FIG. 6b which shows the substrate 12 partially inserted. As the rounded protrusions P reach side wall 50e', their sloping edges P-1 slide along the edge of side wall 50e'. Ultimately, the protrusions P pass side wall 50e' whereupon the straight side P-2 of the protrusions P pass beyond the upper edge of side wall 50e' snap-fittingly locking the heating unit subassembly into the housing.

Figure 2A:
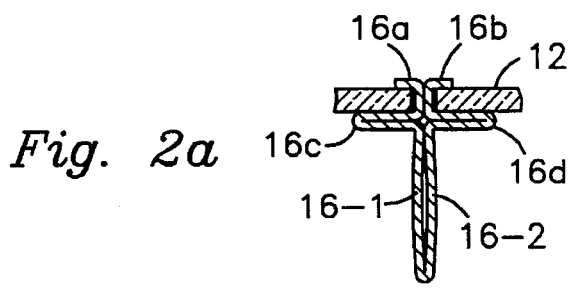
FIG. 2a shows an elevational view, partially sectionalized, of another alternative electrical terminal which may be used in the heating device subassembly of the present invention.

The electrical terminals 16 are formed from a pair of sheet-like members 16-1 and 16-2 which are bent in half and pressed against one another. Each sheet-like conductive member carries one of the prongs 16a and 16b. If desired, each of these members 16-1 and 16-2 may be folded over upon itself to form the supports 16c, 16d shown in FIG. 2a to provide additional support between the terminals and the underside of the substrate. However, it has been found that the combination of the crimped projections 16a, 16b together with the insulating coating which wicks into opening 12a has proven to be more than satisfactory in providing a heating element of superior structural strength and structural and electrical integrity, which may be used in scent and/or repellant emitting devices capable of receiving replacement scent modules.

A latitude of modification, change and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein described.

What is claimed is:

1. A vaporizing device of a simplified, unified design, comprising:

an insulating substrate having a resistance-type electrical heating pattern provided on one major surface thereof, said pattern having heating portions and having first and second terminal ends;

sets of holes being provided in said substrate, each being in the immediate vicinity of an associated one of said terminal ends;

a pair of electrical conductive terminals extending through said openings and outwardly from a major surface of said substrate opposite the surface on which said resistance pattern is provided, said terminals having projecting portions extending outwardly from said one major surface and which are bent over and firmly pressed into intimate engagement with an associated one of said terminal ends to secure the terminals to the substrate and to provide an electrical conductive path between each terminal and an associated terminal end; and an insulating layer being provided over said resistance pattern and exposed surfaces of said bent-over projections to provide an electrical insulating layer, said insulating layer being of a material causing the insulating layer to wick into the said openings and substantially fill the interstices between said openings and said conductive electric terminals to impart significant structural strength to the joined conductive electric terminals and substrate;

a solid module adapted to be vaporized by said heating element when energized;

a cover housing having a hollow interior for receiving said module and being open along one side thereof, said open end being defined by a plurality of side walls each provided with a support shoulder for supporting an associated marginal edge of said substrate;

said housing having openings for enabling vaporized matter to pass out of said housing; and means for securing the marginal edge of said substrate to said housing.

2. The vaporizing device of claim 1 wherein said module is provided with at least one substantially flat surface for positioning adjacent to the surface of said substrate bearing said heating element.

3. The vaporizing device of claim 1 further wherein said openings in said housing are arranged on a surface removed from said heating element.

4. The vaporizing device of claim 3 wherein said openings for emitting vaporized matter are elongated, slot-like openings.

5. The vaporizing device of claim 4 wherein said module has at least one fluted surface cooperating with said slotted openings to provide a chimney effect.

6. The vaporizing device of claim 5 wherein said fluted surface comprises a plurality of undulations.

7. The vaporizing device of claim 4 wherein said housing has openings on a pair of opposing side walls; and said module having at least one fluted surface cooperating with the housing and housing openings to provide a chimney effect.

8. The vaporizing device of claim 1 wherein said electrically conductive terminals formed of a metallic member extend outwardly in a direction perpendicular to a main portion of the terminal to engage a second major surface of said substrate opposite the surface bearing said resistance pattern to further enhance a clamping force between said terminals and said substrate.

9. A vaporizing device of a simplified, unified design, comprising:

an insulating substrate having a layer comprising a resistance-type pattern forming an electrical heater element provided on one major surface thereof;

a pair of electrical conductive terminals each having one end engaging said layer to provide an electrical conductive path between each terminal and said heater element and having an opposite end extending outwardly from a major surface of said substrate opposite the surface on which said resistance pattern is arranged for releasable coupling with an electrical outlet;

a module adapted to be vaporized by said heating element when energized;

a cover housing having a hollow interior for receiving said module and being open along one side thereof;

means for securing a marginal edge about a periphery of said substrate to said housing;

said housing having slotted openings for emitting vapors; and said module having at least one fluted vaporizable surface facing said slotted openings and cooperating with said slotted openings to provide a chimney effect.

10. The vaporizing device of claim 9 wherein said fluted surface comprises a plurality of grooves aligned substantially in parallel and adjacent to an interior wall of said housing containing said slotted openings.

11. A vaporizing device of a simplified, unified design, comprising:

an insulating substrate having a resistance-type electrical layer forming a heater element provided on one major surface thereof, said layer having heating portions and having first and second terminal ends;

sets of holes being provided in said substrate, each being in an immediate vicinity of an associated one of said terminal ends;

a pair of electrical conductive terminals for releasable coupling with an electrical outlet and extending outwardly from a major surface of said substrate opposite the surface on which said resistance pattern is provided, said terminals having projecting portions extending outwardly from said one major surface and which are bent over and firmly pressed into intimate engagement with an associated one of said terminal ends to secure the terminals to the substrate and to provide an electrical conductive path between said terminals and said end;

an insulating layer being provided over said heater element and exposed surfaces of said bent-over projections to provide an electrical insulation and corrosion resistance layer, said insulating layer being of a material that wicks into the said openings and substantially fills interstices between said openings and said conductive electric terminals to provide significant structural strength to the joined conductive terminals and substrate;

a solid module positioned adjacent to and vaporized by said heating element when energized;

a cover housing having a hollow interior for receiving said module and being open along one side thereof, said opening being defined by two pairs of parallel side walls;

one of said pairs of parallel side walls having grooves for slidably receiving opposite parallel edges of said substrate;

one side wall of the remaining pair of parallel side walls extending between said grooved side walls and being of a reduced height to permit insertion of said heating element substrate into said grooves; and one surface of said substrate having at least one protrusion which snap-fittingly locks said substrate into the fully assembled position and engages an interior surface of the side wall of reduced height to retain the substrate in the assembled position within said cover housing.

12. The vaporizing device of claim 11 wherein said protrusion comprises an inclined surface for initially engaging an edge of said cover housing side wall of reduced height, said trailing end of said inclined surface terminating in a trailing surface portion substantially perpendicular to the plane of said substrate for locking said substrate into the assembled position in said housing.

* * * * *

UNITED STATES PATENT AND TRADEMARK OFFICE
CERTIFICATE OF CORRECTION

PATENT NO. : 5,522,008
DATED      : May 28, 1996
INVENTOR(S) : Bernard J. Costello It is certified that error appears in the above-indentified patent and that said Letters Patent is hereby corrected as shown below:

On the title page, under item [19], "Bernard" should read --Costello--; and item [76], Costello J. Bernard" should read --Bernard J. Costello--.

Signed and Sealed this

Third Day of September, 1996

Attest:

BRUCE LEHMAN

*Attesting Officer*      Commissioner of Patents and Trademarks